United States Patent [19] [11] 4,416,899
Umezawa et al. [45] Nov. 22, 1983

[54] ANTIBIOTIC BMG162-AF2, A PROCESS FOR PRODUCTION THEREOF, AND ANTITUMOR DRUG CONTAINING SAID NEW ANTIBIOTIC AS ACTIVE INGREDIENT

[75] Inventors: Hamao Umezawa; Tomio Takeuchi; Hiroshi Naganawa; Hironobu Iinuma; Setsuko Kunimoto, all of Tokyo, Japan

[73] Assignee: Zaidan Hojin Biseibutsu Kagaku Kenkyu Kai, Tokyo, Japan

[21] Appl. No.: 297,458

[22] Filed: Aug. 28, 1981

[30] Foreign Application Priority Data

Sep. 8, 1980 [JP] Japan .................. 55-123585

[51] Int. Cl.$^3$ ...................... A61K 31/16; C12P 21/00; C12R 1/07
[52] U.S. Cl. .................. 424/320; 564/159; 435/129; 435/832
[58] Field of Search .............. 564/159; 424/320; 435/68, 70, 832

[56] References Cited
U.S. PATENT DOCUMENTS 4,163,796 8/1979 Burk .................. 424/320
4,226,808 10/1980 Nagabhushan ............ 424/320
4,328,229 5/1982 Fujii et al. .................. 424/251

OTHER PUBLICATIONS

Shoji et al., J. Antibiotics, vol. 29, No. 4, 1976, pp. 390–393.
Kido et al., J. Antibiotics, vol. 33, No. 8, 1980, pp. 791–795.

Primary Examiner—Thomas G. Wiseman
Assistant Examiner—Frederick W. Pepper
Attorney, Agent, or Firm—David M. Morse

[57] ABSTRACT

A new antibiotic BMG162-aF2 having the formula

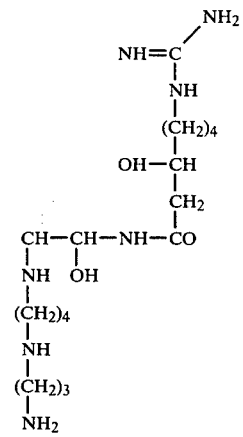

can be obtained by cultivating a BMG162-aF2-producing strain belonging to the genus *Bacillus* in a culture medium to produce and accumulate the said BMG162-aF2 and then recovering it from the culture medium. The antibiotic BMG162-aF2 thus obtained or a pharmaceutically acceptable salt thereof can be used for the treatment of a transplanted tumor in warmblooded animals.

10 Claims, No Drawings

ANTIBIOTIC BMG162-AF2, A PROCESS FOR PRODUCTION THEREOF, AND ANTITUMOR DRUG CONTAINING SAID NEW ANTIBIOTIC AS ACTIVE INGREDIENT

This invention relates to a new antibiotic BMG162-aF2 having the formula

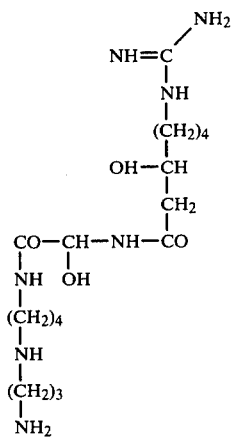

or a pharmaceutically acceptable salt thereof, a process for production thereof, a pharmaceutical composition for inhibiting the growth of transplanted tumors sensitive to antibiotic BMG162-aF2 containing the said antibiotic as an active ingredient and a method for treating a transplanted tumor in a warmblooded animal comprising administering to the said animal a pharmacologically effective amount of the said antibiotic.

BMG162-aF2 is a substance which is obtained by cultivating a BMG162-aF2-producing-strain belonging to the genus Bacillus in a culture medium to produce and accumulate BMG162-aF2 and then recovering BMG162-aF2 from the resulting culture.

As an example of a BMG162-aF2-producing strain belonging to the genus Bacillus, there is a strain of Bacillus BMG162-aF2 which was isolated from a soil sample collected at Mt. Taihei in Tochigi Prefecture, Japan, in August 1978, by the present inventors.

Cultural and taxonomic characteristics of the above-mentioned BMG162-aF2 strain are described below.

1. Microscopic morphology

BMG162-aF2 strain is a Bacillus showing inconstant Gram reaction and having a pore and rod thereof which usually measures 0.6–0.8 by 2–3.5 microns in size. It also has lateral flagella and exhibits active motility. A spore is elliptical, the dominant position thereof being central, and measures 0.5–0.7 by 1.0–1.5 microns in size. The rod is clearly swollen. A spore has in its side part a portion (parasporal body) which stains well in a canoe-shape with crystal violet. The spore is heat-resistant and is not stained with acid-fast staining.

2. Characteristics of the growth on various culture media

All the incubations other than that on nutrient gelatin stab were performed at 37° C.

(1) On a plate of nutrient agar:

Colonies were opaque, dull and round-shaped, and the margin thereof was irregular and appears brownish white.

(2) On a slant of nutrient agar:

Growth diffused and multiplied on the surface of the slant and the surface thereof seemed to be opaque and dry. The color of growth was brownish white.

(3) In nutrient broth:

The culture medium became turbid in its entirety on the 1st day of incubation and the 2nd day a pellicle started to grow on the surface. On the 3rd day, the pellicle overspread the surface and the medium became clear and mycelium was precipitated at the bottom of test tube.

(4) On nutrient gelatin stab:

When incubated at 20° C., multiplication appeared along the stab on the 1st day. On the 2nd day depression started at the said multiplying portion. The gelatin in the medium started to liquefy from about the 6th day. On the other hand, when incubated at 30° C., a pellicle started to grow on the 2nd day and the medium started to liquefy on the 4th day. The liquefaction of gelatin in the medium was completed on the 7th day.

(5) On BCP milk:

From about the 5th day's incubation, bromcresol purple (BCP) turned into blue and from about the 12th day peptonization started.

(6) On Sabouraud dextrose agar and in Sabouraud dextrose broth:

On the slant of Sabouraud dextrose agar (comprising 10 g of peptone, 40 g of dextrose, 15 g of agar and 1,000 ml of deionized water and being pH unadjusted) and in Sabouraud dextrose broth (comprising the same materials as above but with agar being excluded) at 30° C. and 37° C., no growth was observed in liquid medium and the faint growth appeared on the slant at the lower part thereof.

3. Physiological properties

Unless otherwise specifically stated the temperature of incubation was 37° C.

(1) Reduction of nitrate:

On the medium of nitrate broth (comprising 10 g of meat extract, 10 g of peptone, 5 g of NaCl, 1 g of $KNO_3$ and 1,000 ml of deionized water and being pH 7.2), nitrite was detected in all the culture broths on the 1st, 3rd, and 5th day of incubation. On the 5th day, a specifically notable reaction was observed and when a reagent was added to the cultured broth, reddish brown precipitate appeared.

(2) Denitrification reaction:

When the denitrification reaction test was conducted by the method of Komagata et al. (T. Hasegawa, "Toxonomy and Identification of Microorganisms", p. 233, The University of Tokyo Press, 1975), the result was negative.

(3) MR test:

On the culture medium comprising 5 g of glucose, 7 g of peptone, 5 g of NaCl and 1,000 ml of deionized water and being pH 7.5 at 30° C., on the 1st, 2nd and 5th day, the methyl red (MR) test was conducted and gave positive results in all the cases tested.

(4) VP test:

On the culture medium comprising 5 g of glucose, 7 g of peptone, 5 g of NaCl and 1,000 ml of deionized water and being pH 7.5 at 30° C., on the 1st, 2nd and 5th day, the Voges-Proskauer (VP) test was conducted and gave negative results in all the cases tested.

(5) Formation of indole:

On the culture medium comprising 20 g of polypeptone, 5 g of NaCl and 1,000 ml of deionized water and being pH 7.4, on the 1st and 2nd day the formation of indole was not observed and on the 5th day it was observed.

(6) Formation of hydrogen sulfide:

On TSI agar (Triple sugar iron agar: beef extract 3 g, yeast extract 3 g, peptone 15 g, proteose peptone 5 g, lactose 10 g, sucrose 10 g, dextrose 1 g, ferrous sulfate 0.2 g, sodium chloride 5 g, sodium thiosulfate 0.3 g, agar 12 g, phenol red 0.024 g and distilled water 1 L; pH 7.2) for a period of 7 days' incubation, no formation of hydrogen sulfide was observed.

(7) Hydrosis of starch:

On a plate of nutrient agar containing 0.2% soluble starch, cultivation by streaking and testing by iodine-potassium iodide solution were conducted on the 1st, 2nd, 3rd, 5th, 6th, 13th and 15th day, and no decomposition of starch was observed in all the cases.

(8) Utilization of citric acid:

On Koser citrate medium and Christensen agar for 5 days, no growth was observed on both media.

(9) Utilization of inorganic nitrogen sources for growth:

Tests by adding the nitrogen sources [1 g of NaNO$_3$, 0.78 g of (NH$_4$)$_2$SO$_4$ or 1.7 g of sodium glutamate] to the basic medium (comprising 10 g of glucose, 1 g of KH$_2$PO$_4$, 0.5 g of MgSO$_4$.7H$_2$O, 0.2 g of KCl and 1,000 ml of deionized water and being pH 7.2) were conducted, and no growth was observed with all nitrogen sources tested.

(10) Formation of pigment:

After over-night incubation on King's A agar (peptone 20 g, magnesium chloride, 1.4 g, ammonium sulfate 10 g, agar 15 g and distilled water 1 L; pH 7.2), the culture was allowed to stand at room temperature for 6 days, and on King's B agar (peptone 20 g, potassium phosphate, dibasic 1.5 g, magnesium sulfate 1.5 g, agar 15 g and distilled water 1 L; pH 7.2) for 6 days. No soluble pigment was observed in either case.

(11) Urease:

On Urease medium (peptone 2 g, urea 30 g, sodium chloride 5 g, potassium phosphate, monobasic 9 g, sodium phosphate, dibasic 3 g, phenol red 0.01 g and distilled water 1 L; pH 6.2) for 24 hours, the result was urease negative.

(12) Oxidase:

Fresh culture on a slant of nutrient agar over-night showed positive oxidase reaction by Cytochrome oxidase paper (manufactured by Nissui Co.).

(13) Catalase:

Fresh culture on a slant of nutrient agar over-night formed foams and showed positive reaction by catalase test using 3% aqueous hydrogen peroxide.

(14) Conditions of growth:

Tested for 24 hours on nutrient broth at pH 3.0, 4.0, 5.0, 6.0, 6.8, 7.8, 8.2 and 8.8 after sterilization, the growth was observed at pH 5.0 and pH 8.2. Optimum pH for growth is to be pH 6.0–7.8. Tested at 9°, 15°, 20°, 24°, 27°, 30°, 37°, 40°, 45° and 50° C. for 24 hours' incubation, the growth was observed at between 15° and 40° C. Optimum temperature for growth is to be in the vicinity of 37° C.

(15) Effect of oxygen:

When the culture was suspended in nutrient agar containing 1% glucose and hardened as a deep layer agar, good growth was observed around the surface of the medium. On TEP agar (plant extract 7 g, yeast extract 5 g, meat extract 3 g, peptone 10 g, tripton 10 g, soy peptone 3 g, dextrose 3 g, potassium phosphate, monobasic 2.5 g, sodium chloride 2 g, L-cysteine.HCl 0.3 g, sodium thioglycolate 0.3 g, agar 14 g and distilled water 1 L; pH 7.2) under anaerobic conditions, growth was observed.

(16) O-F test (Hugh-Liefson test):

In both cases under aerobic and anaerobic conditions, glucose was decomposed and acid was formed.

(17) Utilization of carbon sources:

When the utilization of carbon compounds was examined by using the method of Iizuka and Komagata (T. Hasegawa, "Toxonomy and Identification of Microorganisms", p. 230, The University of Tokyo Press, 1975), glucose, glycerin and sodium succinate were utilized for growth, while sodium acetate, sodium citrate and sodium parahydroxybenzoate were not utilized.

(18) Formation of acid and gas from sugars:

BMG162-aF2 strain was streaked on the slants which were prepared by added aseptically various sugars sterilized separately to the basic culture media [comprising 1 g of (NH$_4$)$_2$HPO$_4$, 0.2 g of NaCl, 0.2 g of MgSO$_4$.7H$_2$O, 0.2 g of yeast extract, 15 g of agar, 4 ml of 0.2% bromcresol purple aqueous solution and 1,000 ml of deionized water and being pH 7.2] at 1% of the final concentration of each sugar and thereafter coagulating. The formation of acid was examined for a period of 40 days. Acid was formed from D-glucose, D-mannose, D-fructose, D-mannite, maltose, trehalose and glycerin, but not from D-xylose, L-arabinose, D-galactose, rhamnose, D-sorbit, inosite, lactose, sucrose, raffinose and starch.

On the other hand, the formation of gas was examined by using a Durham tube after adding various sugars in the same manner as mentioned above to the basic media (comprising 10 g of peptone, 5 g of NaCl, 0.008 g of bromthymol blue and 1,000 ml of deionized water and being pH 7.2) for 2 weeks. No gas was formed from any of the sugars tested.

(19) Oxidation test of glucronic acid:

Using Glucronate medium (potassium phosphate, monobasic 2 g, magnesium sulfate 0.5 g, sodium chloride 5 g, ammonium sulfate 0.5 g, potassium gluconate 10 g and distilled water 1 L; pH 6.3), the test was negative.

(20) Formation of dihydroxy acetone:

After incubation of the culture medium comprising 10 g of yeast extract, 20 g of glycerin, 15 g of agar and 1,000 ml of deionized water and being pH 7.0 for 3, 5, 10 and 24 days, the formation of dihydroxyacetone was not observed in all the cases tested by Fehling's reagent.

(21) Resistance to sodium chloride:

After inoculation of the strain to the culture media made by adding sodium chloride to the basic culture medium comprising 10 g of trypticase (Trypticase, BBL), and 1,000 ml of deionized water, pH 7.0 so that the concentration of sodium chloride in each culture medium was 2, 5 and 7%, multiplication of the strain on surface culture was observed for a period of 4 days. In the basic culture medium with 2% sodium chloride, the multiplication of the strain was observed, but with more than 2% of the sodium chloride, the growth was not observed.

(22) Decomposition test of hippuric acid:

By incubating on the culture medium (pH 7.4) made by adding 10 g of sodium hippurate to the 1,000 ml of Heart infusion broth (Difco) for 4 days, decomposition of hippuric acid was observed using ferric chloride solution.

(23) Phenylpyruvic acid (PPA) test:

After thickly inoculating the slant comprising 3 g of yeast extract, 2 g of DL-phenylalanine, 1 g of NaHPO$_4$, 5 g of NaCl, 12 g of agar and 1,000 ml of deionized water and having pH 7.3, and thereafter incubating for 24 hours, the test using 10% ferric chloride solution was negative.

(24) Dissolving test of tyrosine:

When incubated on tyrosine agar (comprising 1,000 ml of nutrient agar and 5 g of tyrosine, pH 7.2) at 30° C. and 37° C., the dissolving of tyrosine was observed after 2 to 4 days' incubation.

Summarizing the above-mentioned properties the following are noted:

BMG162-aF2 strain is a Bacillus which is facultative anaerobic and shows inconstant Gram reaction. The strain has spores and lateral flagella and exhibits motility. A spore is elliptical, the dominant portion being central with a portion in its side part (parasporal body) which stains well with crystal violet in a canoe-shape. The spore is also heat-resistant. Rods are clearly swollen and non-acid-fast, and the strain diffuses and multiplies on the agar medium and forms a pellicle in the fluid culture medium. It liquefies gelatin and peptonizes BCP milk after turning into blue. No growth is observed on the Sabouraud dextrose broth, but faint growth is observed on the Sabouraud dextrose agar. It reduces nitrate and the denitrification reaction thereof is negative. The MR test is positive and the VP test is negative. Indole is detected on the 5th day and hydrogen sulfide is not formed. It does not decompose starch and does not utilize citric acid. The results of urease, oxidase and catalase tests are negative, positive and negative, respectively. The growht is observed within the range between pH 5.0 and pH 8.2 and the optimum pH for growth is to be 6.0–7.8. The growth is also observed within the range at 15° C. and 40° C. and the optimum temperature for growth is to be about 37° C. The growth is also observed under aerobic conditions. It decomposes glucose under oxidative and fermentative conditions and forms acid. It forms acid and no gas from D-glucose, D-mannose, D-fructose, D-mannite, maltose, trehalose and glycerin. It neither oxidizes glucronic acid nor forms dihydroxyacetone. It does not decompose hippuric acid and phenylalanine and dissolves tyrosine. The growth is not observed in the culture medium with more than 5% of sodium chloride.

On the basis of the above characteristics of the strain BMG162-aF2, it is concluded that this strain belongs to the genus Bacillus and especially to *Bacillus firmn, B. laterosporus, B. brevis* or *B. sphaericus*, which are a group of species having common characteristics: catalase positive and dihydroxyacetone not produced, as described in Bergey's Manual of Determinative Bacteriology, Eighth Edition, page 542 (R. E. Buchanan and N. E. Gibbons, The Williams & Wilkins Company, Baltimore, 1974). Compared with the above four species, the character of strain BMG162-aF2 is shown in Table 1.

As seen in Table 1, the strain BMG162-aF2 is very similar to *Bacillus laterosporus*. The differentiation between the strain BMG162-aF2 and *B. laterosporus* is that one merely differs from the other in the description of the appearance of growth on the Sabouraud glucose agar.

TABLE 1

Comparison of BMG162-aF2 strain and its related species

| | B. firmus | B. laterosporus | B. brevis | B. sphaericus | BMG162-aF2 |
|---|---|---|---|---|---|
| Spore | | | | | |
| Shape | E[a] | E | E | S | elliptical |
| Distends sporangium districtly | − | + | + | + | + |
| Dominant position | C | C | CT | T | C |
| Formation from glucose | | | | | |
| Acid | + (week) | + | + or − | − | + |
| Gas | − | − | − | − | − |
| Acetoin | − | − | − | − | − |
| Rods | | | | | |
| Width, μm | 0.6–0.9 | 0.5–0.8 | 0.6–0.9 | 0.6–1 | 0.6–0.8 |
| Length, μm | 1.2–4 | 2–5 | 1.5–4 | 1.5–5 | 2–3.5 |
| Gram reaction | + | d and v | d and v | d and v | d and v |
| Easily stainable body attached to one side of spore | − | + (+)[b] | − | − | + |
| Motility | d | + | + | + | + |
| Temperature for growth, °C. | | | | | |
| Maximum | 40–45 | 35–50 | 40–60 | 30–45 | 40 |
| Minimum | 5–20 | 15–20 | 10–35 | 5–15 | 15 |
| Acid from | | | | | |
| Arabinose and xylose | d | − | − | − | − |
| Mannitol | + | + | d | − | + |
| Hydrolysis of starch | + | − | − | − | − |
| Growth in | | | | | |
| Anaerobic agar | − | + | − | − | + |
| 7% NaCl | + | − | − | d | − |
| Sabouraud dextrose broth | − | −(±)[b] | d | d | ± |
| Sabouraud dextrose agar | | − | | | − |
| Production of Alkaline | | | | | |
| reaction in V-P broth | − | − | + | + | − |
| Formation of indole | − | d | − | − | + at 5 days' culture |
| NO$_3^-$ to NO$_2^-$ | + | + | d | − | + |
| Decomposition of | | | | | |
| Casein | + | + | + | d | + |
| Tyrosine | d | + | + | − | + |

TABLE 1-continued

Comparison of BMG162-aF2 strain and its related species

| | B. firmus | B. laterosporus | B. brevis | B. sphaericus | BMG162-aF2 |
|---|---|---|---|---|---|
| Deamination of phenylalanine | d | — | — | + | — |

<sup>a</sup>E = elliptical or cyclindrical; S = spherical or nearly so; C = central; T = terminal or subterminal; CT = central to terminal; variation within or between strains; + = positive for 90–100% of strains; — = negative for 90–100% of strains; d = reactions differ, positive for 11–89% of strains; v = character inconstant in one strain.
<sup>b</sup>The experimental result.

Upon being given a strain of *B. laterosporus* by Dr. Ryozo Azuma of the National Institute of Animal Health, Japan, the present inventors examined and compared it with the BMG162-aF2-producing strain of the present invention. As a result, the inventors can verify that both strains have a canoe-shaped body (a portion stained in canoe-shape; parasporal body) in the side part of their spores, which is a characteristic feature of this species. Also, the growth on Sabouraud-dextrose agar of both strains is coincident with each other. In view of the above, the strain BMG162-aF2 has been assigned as *Bacillus laterosporus* BMG162-aF2.

Furthermore, this BMG162-aF2 strain was deposited on Oct. 12, 1979 in the Japanese authorized depository "Fermentation Research Institute, Agency of Industrial Science and Technology", Inage, Chiba-City, Japan, under deposit number FERM-P 5230, and then deposited on July 31, 1981 in the American Type Culture Collection, Parklawn Drive, Rockville, Md., U.S.A., under deposit number ATCC 31932.

It will be appreciated by those skilled in the art that, given our invention, it should now be possible to generate additional strains of Bacillus which have essentially the same biosynthetic capabilities as *B. laterosporus* ATCC 31932 (i.e. the ability to produce BMG162-aF2) by subjecting *B. laterosporus* ATCC 31932 to mutagenic treatment, e.g. by use of mutagens such as ultraviolet rays, x-rays, high-frequency waves, radioactive rays and chemicals. All natural and artificial variants and mutants of ATCC 31932 which have essentially the same biosynthetic capabilities of ATCC 31932 are therefore encompassed by the present invention.

Production of the Antibiotic

The antibiotic BMG162-aF2 may be prepared by fermentation of BMG162-aF2-producing strains of Bacillus. Production is carried out by cultivating the appropriate producing strain, preferably *Bacillus laterosporus* BMG162-aF2 (FERM-P5230; ATCC 31932) or a mutant thereof, in a conventional aqueous nutrient medium containing known nutrient materials. Submerged aerobic cultivation of spores or rods of the producing strain is preferably employed for the production of substantial amounts of the BMG162-aF2 antibiotic. Generally, nutrient constituents of the culture media commonly employed for fermentation of other bacteria may be used in the process of the present invention. For example, commercially available peptone, meat extract, corn steep liquor, cotton seed meal, peanut meal, soybean meal, yeast extract, N-Z amine, hydrolysate of casein, sodium nitrate, ammonium nitrate, ammonium sulfate and the like may be useful as the assimilable nitrogen source. Commercially available glycerin, sucrose, starch, glucose, maltose, molasses and other carbohydrates as well as fat and oil are useful as the assimilable carbon source. In addition, sodium chloride, phosphates, calcium carbonate, magnesium sulfate and other inorganic salts can be employed for the salt-additive in the culture medium. Other metal salts may also be added in trace quantities, if required, as long as they are utilized by the BMG162-aF2-producing strain and are not detrimental to the production of BMG162-aF2. Any of the nutrient materials which are known for cultivation of bacteria may be employed in the process of this invention, as far as they are assimilable by the BMG162-aF2-producing strain for the production of BMG162-aF2.

For the production of BMG162-aF2 on a large scale, liquid cultivation is preferred. Any temperature at which the BMG162-aF2-producing strain is able to grow and produce BMG162-aF2 can be employed for the cultivation, but a particularly preferred incubation temperature is in a range of 20° C. to 35° C. The pH of the medium is 5.0 to 8.2, and a preferred pH is in a range of 6.0 to 7.8. The cultivation is continued for a period of time sufficient to produce and accumulate a sufficient amount of BMG162-aF2 in the culture medium or broth. For instance, the production and accumulation of BMG162-aF2 was observed after a one day incubation when a liquid culture medium comprising 2.0% glycerine, 2.0% glucose, 1.0% peptone, 0.3% yeast extract, 0.2% calcium carbonate (the most suitable pH is about 7.4) was prepared and sterilized, followed by inoculation with spores and rods harvested from a slant culture of the BMG162-aF2 strain and by rotary-shake-cultivation at 27° C. under aerobic conditions.

For production of relatively small amounts of antibiotic, shake flasks and jars can be employed, but for large scale production, submerged aerobic culture in sterile tanks is preferred. When tank fermentation is to be carried out, it is desirable to produce a vegetative inoculum in a nutrient broth by inoculating the broth culture with a rod or spore of the producing organism and, when a young active vegetative inoculum has been obtained (e.g. after 20–40 hours shake-cultivation), transferring the inoculum aseptically to the fermentation tank medium, preferably at 0.5 to 2% volume. Aeration in tanks and jars may be provided by forcing sterile air through or onto the surface of the fermenting medium. Further agitation in tanks is generally provided by a mechanical impeller. An antifoaming agent such as lard oil may be added as needed.

Assay of BMG162-aF2 can be made using *Bacillus subtilis* PCI 219 as the test organism according to a standard cup-plate method which has conventionally been employed for the assay of known antibiotics.

Recovery of BMG162-aF2 from the fermentation broth filtrate may be carried out by means of column chromatography using a weak cationic ion exchange resin having carboxylic acid as an active group. As examples of suitable weak cation exchange resins, there may be used Amberlite IRC-50 ® and CG-50 ® (tradenames for cation exchange resins in which the activity is due to the carboxylic group exclusively, manufactured by Rohm & Haas Co.), Lewatit CNP ® (tradename for a cation exchange resin in which the activity is due to carboxylic acid and sulfonic acid groups, manufactured by Bayer Ltd.) or CM-Sephadex ® (tradename for carboxymethyldextran, a cation exchanger, manufactured by Pharmacia Fine Chemicals) which are available in H-form, Na-form, NH₄-form or mixed form. The BMG162-aF2 adsorbed on the resin is then eluted with an aqueous acid solution such as hydrochloric acid, acetic acid, etc. and/or an aqueous salt solution such as sodium chloride. The antibiotic may be subjected to further purification by conventional methods such as gel filtration, ultrafiltration or ion exchange chromatography to obtain BMG162-aF2 in a highly purified form.

Since BMG162-aF2 is unstable in the form of the free base, it is preferred to recover the antibiotic in the form of an acid addition salt, most preferably the hydrochloride, by adding the appropriate acid during the recovery procedure. The hydrochloride salt is so hydroscopic that it forms a hydrate. The physicochemical properties of the preferred BMG162-aF2 hydrochloride hydrate are as follows:

Because of the extreme hydroscopicity of the hydrochloride salt, it is impossible to measure its melting point. It exhibits $[\alpha]_D^{24} = -11°$ (c=1.0, water). Anal. Found: C 37.55, H 7.89, N 17.52, Cl 18.61. Calc'd for $C_{17}H_{37}N_7O_4 \cdot 3HCl \cdot 2H_2O$: C 37.20, H 8.08, N 17.86, Cl 19.38. The $^1$H-NMR and $^{13}$C-NMR spectra are consistent for the BMG162-aF2 structure shown above. In the $^{15}$N-NMR spectrum, seven nitrogen atoms are observed (3 nitrogen atoms in guanidyl groups are observed as 2 peak signals). The ultraviolet absorption spectrum has only end absorption. The infrared spectrum is consistent for the indicated structure of the antibiotic.

As indicated above BMG162-aF2 is a basic antibiotic capable of forming salts with acids, and pharmaceutically acceptable acid addition salts of the antibiotic are included within the present invention. "Pharmaceutically acceptable" salts are salts in which the toxicity of the compound as a whole in warm-blooded animals is not increased relative to the non-salt form. Examples of suitable pharmaceutically acceptable acid addition salts include those salts formed by standard reaction with both organic and inorganic acids such as hydrochloric, sulfuric, phosphoric, acetic, succinic, citric, lactic, maleic, fumaric, palmitic, formic, stearic, propionic, tartaric, benzoic, salicylic, methanesulfonic, benzenesulfonic, cinnamic and the like. As an example of salt formation, the free base compound may be dissolved in water, treated with the desired acid and lyophilized. For purposes of the present invention, the free base form and pharmaceutically acceptable acid addition salts are equivalent.

BMG162-aF2 hydrochloride is easily soluble in water and methanol, but only slightly soluble or insoluble in ethanol, ethyl acetate, chloroform and benzene. It gives positive ninhydrin, Sakaguchi and Rydon-Smith reactions. On thin layer chromatography using Avicel® (microcrystalline cellulose) and developing with butanol-pyridine-acetic acid-water (6:4:1:3) (v/v) and butanol-ethanol-water (4:1:2) (v/v), BMG162-aF2 hydrochloride exhibits a single spot at Rf=0.14 and RF=0.20, respectively. On high voltage paper electrophoresis (3,500 V, 15 minutes) using formic acid-acetic acid-water (1:3:36) (v/v), BMG162-aF2 shows relative mobility at 1.70–1.74 to alanine as 1.00.

Biological Properties

As shown below, BMG162-aF2 (as the hydrochloride salt) has only weak inhibitory activity against Gram-positive and Gram-negative bacteria. On the othe hand, it exhibits remarkable effects of cure and elongation of survival period in experiments using mouse leukemia L-1210, EL-4, Ehrlich ascites tumor and Sarcoma 180. Therefore, the antibiotic of the present invention and its pharmaceutically acceptable acid addition salts are useful as antitumor agents in warm-blooded animals.

(1) Antibacterial activity of BMG162-aF2

BMG162-aF2 has weak antibacterial activity, and the minimum inhibitory concentration to various bacteria on nutrient agar is shown in Tables 2-1 to 2-3. The test was carried out by the agar dilution method using BMG162-aF2 hydrochloride. As seen in Table 2-1, BMG162-aF2 weakly inhibits Gram positive and negative bacteria.

TABLE 2-1

Antibacterial Activity

| Test Organism | Minimum inhibitory concentration (mcg/ml) |
|---|---|
| 1. Staphylococcus aureus FDA209P | 100 |
| 2. Staphylococcus aureus Smith | 12.5 |
| 3. Micrococcus flavus FDA16 | 25 |
| 4. Micrococcus lysodeikticus IFO3333 | 100 |
| 5. Sarcina lutea PCI1001 | 100 |
| 6. Bacillus anthracis | 25 |
| 7. Bacillus subtilis NRRL B-558 | 100 |
| 8. Bacillus subtilis PCI219 | 6.25 |
| 9. Bacillus cereus ATCC 10702 | >100 |
| 10. Corynebacterium bovis 1810 | 50 |
| 11. Escherichia coli NIHJ | >100 |
| 12. Escherichia coli K-12 | 100 |
| 13. Escherichia coli ML1629 | >100 |
| 14. Shigella dysenteriae JS11910 | 100 |
| 15. Shigella flexneri 4bJS11811 | >100 |
| 16. Shigella sonnei JS11746 | >100 |
| 17. Salmonella typhi T-63 | >100 |
| 18. Salmonella enteritidis | >100 |
| 19. Proteus vulgaris OX19 | 12.5 |
| 20. Proteus mirabilis IFM OM-9 | >100 |
| 21. Proteus rettgeri GN311 | >100 |
| 22. Proteus rettgeri GN466 | >100 |
| 23. Serratia marcescens | >100 |
| 24. Pseudomonas aeruginosa A3 | >100 |
| 25. Klebsiella pneumoniae PCI602 | >100 |
| 26. Mycobacterium smegmatis ATCC 607 | >100 |

Medium used: nutrient agar at 37° C.

TABLE 2-2

Antibacterial Activity

| Test Organism | Minimum inhibitory concentration (mcg/ml) |
|---|---|
| 1. Aeromonas punctata IAM1646 | >100 |
| 2. Aeromonas salmonecida ATCC 14174 | >100 |
| 3. Aeromonas sp. (KT-444) | >100 |
| 4. Vibrio anguillarum NCBM6 | 50 |
| 5. Pseudomonas fluorescens | >100 |
| 6. Pseudomonas lachrymans | 50 |
| 7. Erwinia aroideae | 50 |

Medium used: nutrient agar At 27° C.

TABLE 2-3

Antibacterial Activity

| Test Organism | Minimum inhibitory concentration (mcg/ml) |
|---|---|
| 1. Candida tropicalis F-1 | >100 |
| 2. Candida pseudotropicalis NI7494 | >100 |
| 3. Candida albicans 3147 | >100 |
| 4. Candida Yu-1200 | >100 |
| 5. Candida krusei NI7492 | >100 |
| 6. Saccharomyces cerrevisiae | >100 |
| 7. Cryptococcus neogormans | >100 |
| 8. Helminthosporium oryzae | >100 |

TABLE 2-3-continued

| Antibacterial Activity | |
|---|---|
| Test Organism | Minimum inhibitory concentration (mcg/ml) |
| 9. *Pyricularia oryzae* | >100 |
| 10. *Pellicularia filamentosa sasakii* | >100 |
| 11. *Xanthomonas citri* | >100 |
| 12. *Xanthomonas oryzae* | >100 |
| 13. *Aspergillus niger* | 100 |
| 14. *Trichophyton asteroides* 429 | >100 |
| 15. *Trichophyton mentagrophytes* | >100 |

Medium used: nutrient agar + 1% glucose at 27° C.

(2) BMG162-aF2 activity against transplanted tumors (a) Effect on mouse leukemia L1210 (ip—ip system)

To a group comprising 8 $CDF_1$ mice (female, 6–7 weeks old), $10^5$ cells/0.25 ml/mouse of L1210 leukemia cells were inoculated intraperitoneally. After 24 hours, BMG162-aF2 hydrochloride dissolved in saline was dosed intraperitoneally once a day for 9 days continuously, and the lethality and the rate of elongation of survival period were determined. As shown in Table 3, BMG162-aF2 showed a curative effect and an effect of elongation of survival period with mouse leukemia L1210.

TABLE 3

Effect of BMG162-aF2 on mouse leukemia L1210 (ip-ip system)

| Dose (mg/kg/day) | $\frac{\text{Average survival days of treated}}{\text{Average survival days of control}} \times 100$ | No. of mice survival for 60 days / No. of mice tested |
|---|---|---|
| 50 | 295* | 0/8 |
| 25 | 334 | 0/8 |
| 12.5 | 586 | 4/8 |
| 6.25 | 732 | 8/8 |
| 3.13 | 441 | 3/8 |
| 1.56 | 301 | 1/8 |
| 0.78 | 107 | 0/8 |

*Toxic sign appeared
Average survival days of control: 8.2 days (b) Effect on mouse leukemia L1210 (sc-ip system)

A group of 5 $CDF_1$ mice (female, 6–7 weeks old) was injected with mice leukemia cells L1210 ($10^5$ cells/0.25 ml/mouse) to the side of the abdomen subcutaneously. After 24 hours, the mice were treated with BMG162-aF2 hydrochloride in saline intraperitoneally once a day for 9 days continuously. The lethality and the rate of elongation of survival period were then determined. As shown in Table 4, BMG162-aF2 showed a strong therapeutic effect and an elongation of survival period equal to that in experiment (a).

TABLE 4

Effect of BMG162-aF2 on mouse leukemia L1210 (sc-ip system)

| Dose (mg/kg/day) | $\frac{\text{Average survival days of treated}}{\text{Average survival days of control}} \times 100$ | No. of mice survival for 30 days / No. of mice tested |
|---|---|---|
| 50 | >309 | 5/5 |
| 25 | >309 | 5/5 |
| 12.5 | >309 | 5/5 |
| 6.25 | >240 | 3/5 |
| 3.13 | 120 | 0/5 |
| 1.56 | 105 | 0/5 |

Average survival days of control: 9.7 days (c) Effect on mouse leukemia EL-4

A group of 5 $C_{57}BL/6$ mice (female, 10 weeks old) was inoculated with mice leukemia cells EL-4 ($10^5$ cells/0.25 ml/mouse) intraperitoneally, and after 24 hours the mice were treated with BMG162-aF2 hydrochloride in saline intraperitoneally once a day for 9 days continuously. The lethality and the rate of elongation of survival period were determined. As shown in Table 5, BMG162-aF2 exhibited a therapeutic effect and an elongation of survival period with respect to EL-4.

TABLE 5

Effect of BMG162-aF2 on mouse leukemia EL-4

| Dose (mg/kg/day) | $\frac{\text{Average survival days of treated}}{\text{Average survival days of control}} \times 100$ |
|---|---|
| 5 | 193 |
| 2.5 | 164 |
| 1.25 | 159 |
| 0.625 | 130 |
| 0.313 | 131 |

Average survival days of control: 11.0 days (d) Effect on mouse Ehrlich ascites tumor A group of 4 ICR mice (female, 6 weeks old) was inoculated intraperitoneally with Ehrlich ascites tumor cells ($2 \times 10^6$ cells/0.25 ml/mouse), and after 24 hours the mice were treated with BMG162-aF2 hydrochloride in saline by intraperitoneal injection once a day for 9 days continuously. The rate of elongation of survival period was measured. As shown in Table 6, BMG162-aF2 also showed an effect against a transplanted tumor with respect to Ehrlich ascites tumor.

TABLE 6

Effect of BMG162-aF2 on mouse Ehrlich ascites tumor

| Dose (mg/kg/day) | $\frac{\text{Average survival days of treated}}{\text{Average survival days of control}} \times 100$ |
|---|---|
| 50 | 54* |
| 25 | 72* |
| 12.5 | 170* |
| 6.25 | 236 |
| 3.13 | 188 |
| 1.56 | 133 |

*Toxic sign appeared
Average survival days of control: 13.8 days (e) Effect on Sarcoma 180

A group of 4 ICR mice (female, 6 weeks old) was inoculated intraperitoneally with mice Sarcoma 180 cells ($2 \times 10^6$ cells/0.25 ml/mouse), and after 24 hours the mice were treated with BMG162-aF2 hydrochloride in saline by intraperitoneal injection once a day for 9 days continuously. The rate of elongation of survival period was tested. As shown in Table 7, BMG162-aF2 also showed an effect against a transplanted tumor with respect to Sarcoma 180.

TABLE 7

Effect of BMG162-aF2 on mouse Sarcoma 180

| Dose (mg/kg/day) | $\frac{\text{Average survival days of treated}}{\text{Average survival days of control}} \times 100$ |
|---|---|
| 50 | 53* |
| 12.5 | >279* |
| 6.25 | 181* |
| 3.13 | 243 |
| 1.56 | 220 |

*Toxic sign appeared
Average survival days of control: 13.8 days (3) Acute toxicity of BMG162-aF2

When BMG162-aF2 hydrochloride was intravenously injected to ICR mice (female, 4 weeks old), the LD$_{50}$ was more than 80 mg/kg.

The physicochemical and biological properties of BMG162-aF2 have been described in detail above. From the fact that spermidine is a common constituent of the molecule, BMG162-aF2 resembles bleomycin produced by *Streptomyces verticillus*, LL-BM123β, γ$_1$ and γ$_2$ produced by Nocardia, edenine produced by *Bacillus brevis* and laterosporamine produced by Bacillus. Since the structure of BMG162-aF2 has been determined as that shown above, BMG162-aF2 is clearly different from bleomycin, LL-BM123β, γ$_1$ and γ$_2$ and edenine which have known structures. Further, it is differentiated from laterosporamine [The Journal of Antibiotics 29, 390–393 (1976)] in infrared spectrum, solubility in alcohol, antibacterial spectrum and the fact that a Sakaguchi positive substance comprising $C_6H_{13}N_3O$, which is a constituent of laterosporamine, is not contained in decomposition products of BMG162-aF2. Therefore, it is confirmed that BMG162-aF2 is a novel antibiotic.

From the foregoing results, BMG162-aF2 shows an inhibitory effect on the growth of various transplanted tumor systems (e.g. leukemia, sarcoma and other transplanted tumors) in warm-blooded animals and has relatively low toxicity. Therefore, BMG162-aF2 can be used as a drug against transplanted tumors in the treatment of mammalian transplanted tumors.

As for the procedures for pharmaceutical preparation and of administration of BMG162-aF2 as an antitumor drug, various known methods are applicable. For administration of BMG162-aF2, it is possible to use parenteral, oral and rectal administration. For pharmaceutical formulations, injectable preparations, powders, granules, tablets, suppositories, etc. may be utilized.

In the pharmaceutical preparations, any conventional pharmaceutically acceptable carrier such as solid carriers, liquid carriers, stabilizers, antiseptics, anesthetic agents, emulsifiers, etc. can be used if necessary, as long as they are inert to BMG162-aF2. As an example of an injectable pharmaceutical formulation, BMG162-aF2, preferably a water-soluble salt such as the hydrochloride, and a saccarose (a water-soluble saccharide) such as mannitol are dissolved in distilled water and put in small containers (vials), or this solution may further be lyophilized and dissolved in saline or distilled water to make a solution for an injection at the time of administration.

In the pharmaceutical preparations, the proportion of the contents can be varied in a wide range according to the particular preparation, but in general, 0.01 to 100% by weight, preferably 0.1 to 70% by weight of BMG162-aF2 is present and the residual content, that is, 0 to 99.99% by weight, preferably 99.9 to 30% by weight is pharmaceutically acceptable carrier. In the case of an injectable composition, the proportion of the contents may be as follows:

| | |
|---|---|
| BMG162-aF2 | 0.1 to 95.0% by weight |
| Saccarose | 99.1 to 5.0% by weight |
| Sodium chloride | 0 to 94.9% by weight |

Though the particular dosage of BMG162-aF2 varies depending upon the symptoms, 0.01–800 mg/day/adult, preferably 0.1–600 mg/day/adult, are generally used. If it is necessary to administrate continuously, the daily amount should be reduced.

In the pharmaceutical preparations of BMG162-aF2, it is generally preferred to use the antibiotic in the form of its pharmaceutically acceptable acid addition salt such as the hydrochloride, etc.

This invention is illustrated by the following Examples, but the invention is not limited thereto.

EXAMPLE 1

Five liters of liquid medium comprising 2.0% glycerin, 2.0% dextrin, 1.0% soy peptone (Bacto-soytone, produced by Difco Laboratories), 0.3% yeast extract (Daigo-Eiyo-Kagaku Co., Ltd.), 0.2% ammonium sulfate and 0.2% calcium carbonate and being pH 7.4 was placed in 125 ml portions in 500 ml Sakaguchi flasks. After sterilization the flasks were inoculated with 1% of seed medium prepared previously [*Bacillus laterosporus* BMG162-aF2 (FERM-P 5230; ATCC 31932) on a slant of nutrient agar was cultured in the medium of the same composition for 2 days] and cultured at 28° C. for 5 days. Broth filtrate obtained (4900 ml) was poured onto a column (500 ml, diam. 5.2 cm) of Amberlite IRC-50® [Rohm and Haas Co., Na$^+$ type and H$^+$ type (7:3) mixture], and the active component was adsorbed. The column was washed with water, and the active component was eluted with 2000 ml of 1.0 N HCl and neutralized with 10 N NaOH to pH 6. The neutralized solution was diluted 4-fold with water and poured onto a column (400 ml, diam. 4.3 cm) of CM-Sephadex C-25® (Pharmacia Fine Chemicals, swollen by pretreatment with water) on which the active component was adsorbed. The active component was eluted with 0.3 M NaCl-H$_2$O. The active fraction was concentrated to dryness under reduced pressure. The residue was dissolved with 5 ml of methanol to remove crystals of NaCl by filtration. The filtrate was poured onto a column (445 ml, diam. 2.6 cm) of Sephadex LH-20® (tradename for dextran for gel-filtration with organic solvent, manufactured by Pharmacia Fine Chemicals, swollen by pretreatment with methanol), and the column was developed with methanol. The active fraction was dried under reduced pressure to obtain 460 mg of pure BMG162-aF2 hydrochloride as a white powder.

EXAMPLE 2

A medium (10 L) containing 2.0% glycerin, 2.0% dextrin, 1.0% soy peptone (Bacto-soytone®, produced by Difco Laboratories), 0.3% yeast extract (Daigo-Eiyo-Kagaku Co., Ltd.), 0.2% ammonium sulfate, 0.2% calcium carbonate and 0.03% silicone oil for antifoam and having pH 7.4 was put in a stainless tank of 30 L capacity, sterilized at 120° C. for 20 minutes. To the cooled tank 125 ml of 48 hours' shake-cultured broth of BMG162-aF2-producing strain, *Bacillus laterosporus* BMG162-aF2 FERM-P 5230, ATCC 31932, was aseptically inoculated. The cultivation under aeration and stirring at 28° C. was carried out (started at the rate of aeration of 15 L/min and at an agitator speed of 350 r.p.m., after 16 hours at 10 L/min and 350 r.p.m.), and after 40 hours, 9,500 ml of broth filtrate obtained was treated with column chromatographies of Amberlite IRC-50® and CM-Sephadex C-25® in substantially the same manner as in Example 1. The column of CM-Sephadex C-25® was developed with 4 L of 0.3 M-NaCl—H$_2$O. The eluate (290 drops) was collected as one portion, and separated into two active fractions: I (portion No. 14-63) and II (portion No. 64-154). To the 1,660 ml of active fraction II, which does not contain a substance having absorption at 280 nm, there was added 33 g of an active charcoal to adsorb the active ingredient. After the active charcoal was washed with water, BMG162-aF2 was eluted with 500 ml of 0.05 N-HCl in 80% methanol-water. The eluate was neutralized with Amberlite IR-45 ® (Rohm and Haas Co., OH⁻ type), and dried under reduced pressure to yield 305 mg of BMG162-aF2 hydrochloride. The active fraction I containing a substance having an absorption at 280 nm was concentrated to dryness, extracted with methanol, dissolved with 1 liter of deionized water, and rechromatographed with a column (400 ml, diam. 4.3 cm) of CM-Sephadex C-25 ® followed by a gradient elution using 0–1 M-NaCl (4 L) to obtain the active fraction, which was concentrated to dryness. The residue was extracted with methanol and applied to a column (780 ml, diam. 2.8 cm) of Sephadex LH-20 ®. The column was developed with methanol to remove NaCl and to obtain 670 mg of pure BMG162-aF2 hydrochloride. Totally, 975 mg of BMG162-aF2 hydrochloride were recovered.

EXAMPLE 3

To a solution containing 150 mg of BMG162-aF2 hydrochloride obtained in Example 2 dissolved with 1 ml of methanol, 1 ml of saturated picric acid-methanol solution was added and heated to boiling. After concentration, the residue was washed with benzene and ethanol to remove the excess picric acid and 62 mg of crystals of BMG162-aF2 picrate was obtained from a solution of a water-ethanol mixture.

EXAMPLE 4

An injectable formulation

30 Parts by weight of BMG162-aF2 hydrochloride obtained in Example 1 were dissolved in 970 parts of purified water and filtered to make a germ free solution using Millipore filter-GS-type. The filtrate (1 g) was put into a vial of 10 ml capacity and lyophilized to yield a freeze-dried formulation containing 30 mg of BMG162-aF2 hydrochloride.

EXAMPLE 5

A granular formulation

50 Parts by weight of BMG162-aF2 hydrochloride obtained in Example 1, 600 parts by weight of lactose, 330 parts by weight of crystalline cellulose and 20 parts by weight of hydroxypropyl cellulose were thoroughly mixed, compressed using a rolling compressor (Roller-Compactor ®), and crushed to make a granular formulation which was sieved at size between 16 mesh and 60 mesh.

EXAMPLE 6

A tablet formulation

30 Parts by weight of BMG162-aF2 hydrochloride obtained in Example 1, 20 parts by weight by crystalline lactose, 147 parts by weight of crystalline cellulose and 3 parts by weight of magnesium stearate were mixed by using a V-shape-mixer and tablets containing 300 mg of BMG162-aF2 were obtained.

We claim:

1. A antibiotic BMG162-aF2 having the formula

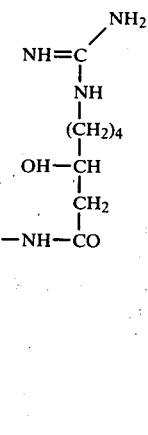

or a pharmaceutically acceptable salt thereof.

2. The hydrochloride salt of the antibiotic of claim 1.

3. A pharmaceutical composition for inhibiting the growth of transplanted tumors sensitive to antibiotic BMG162-aF2 comprising a pharmacologically effective amount of antibiotic BMG162-aF2 having the formula

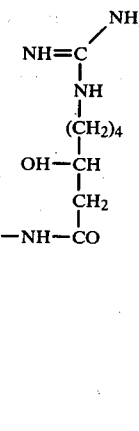

or a pharmacetically acceptable salt thereof and a pharmaceutically acceptable carrier.

4. The composition of claim 3, wherein the proportion of the said antibiotic BMG162-aF2 and the said carrier is 0.1 to 70% by weight and 99.1 to 30% by weight, respectively.

5. The composition of claim 3 or claim 4, which is in the form of an injectable preparation, a powder, a granule, a tablet or a suppository.

6. A composition for injection comprising 0.1 to 95.0% by weight of an antibiotic BMG162-aF2 having the formula

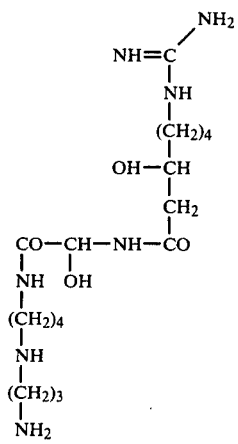

or a water-soluble salt thereof, 5.0 to 99.9% by weight of saccarose and 0 to 94.9% by weight of sodium chloride.

7. The composition of claim 6, wherein the saccarose is mannitol.

8. A method for inhibiting the growth of a transplanted tumor sensitive to antibiotic BMG162-aF2 in a warm-blooded animal comprising administering to said animal a pharmacologically effective amount of an antibiotic BMG162-aF2 having the formula

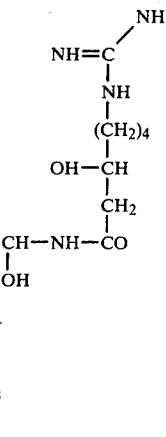

or a pharmacetically acceptable salt thereof.

9. A method according to claim 8, wherein the pharmacologically effective amount is 0.01 to 800 mg/day.

10. A method according to claim 8 or claim 9, wherein the pharamaceutically acceptable salt is the hydrochloride.

* * * * *